United States Patent [19]

Tanaka et al.

[11] Patent Number: 4,837,214
[45] Date of Patent: Jun. 6, 1989

[54] SUPPOSITORY AND BASE THEREOF

[75] Inventors: Yukitaka Tanaka; Minoru Nakamura, both of Ibaraki; Johshin Okada; Kenji Mansho, both of Utsunomiya, all of Japan

[73] Assignee: Kao Corporation, Tokyo, Japan

[21] Appl. No.: 909,664

[22] Filed: Sep. 19, 1986

[30] Foreign Application Priority Data

Sep. 30, 1985 [JP] Japan .................................. 60-217527

[51] Int. Cl.$^4$ ............................................. A61K 31/56
[52] U.S. Cl. .................................... 514/179; 514/786; 514/966
[58] Field of Search ......................... 514/179, 786, 966

[56] References Cited

U.S. PATENT DOCUMENTS

| | | | |
|---|---|---|---|
| 3,594,473 | 7/1971 | Hunger et al. | 514/966 X |
| 4,406,896 | 9/1983 | Higuchi et al. | 514/966 X |
| 4,698,359 | 10/1987 | Niederer et al. | 514/396 |

OTHER PUBLICATIONS

Lachman et al.—"The Theory & Practice of Industrial Pharmacy", 2nd ed., 1976, pp. 250-257.

*Primary Examiner*—Leonard Schenkman
*Attorney, Agent, or Firm*—Flynn, Thiel, Boutell & Tanis

[57] ABSTRACT

A suppository base comprises 80 to 99 percent by weight of a lauric-type fat having a hydroxyl value of 20 or smaller and containing glycerides of fatty acids having 8 to 18 carbon atoms as the main component and 1 to 20 percent by weight of diglycerides of fatty acids having 14 to 22 carbon atoms and provides an improvement in the discharging property of a medicine contained therein.

9 Claims, 1 Drawing Sheet

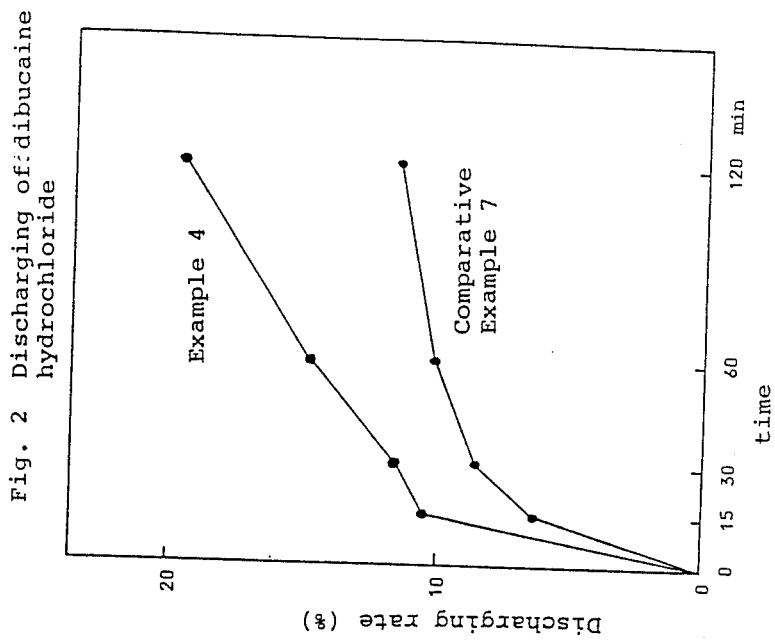
Fig. 2 Discharging of dibucaine hydrochloride
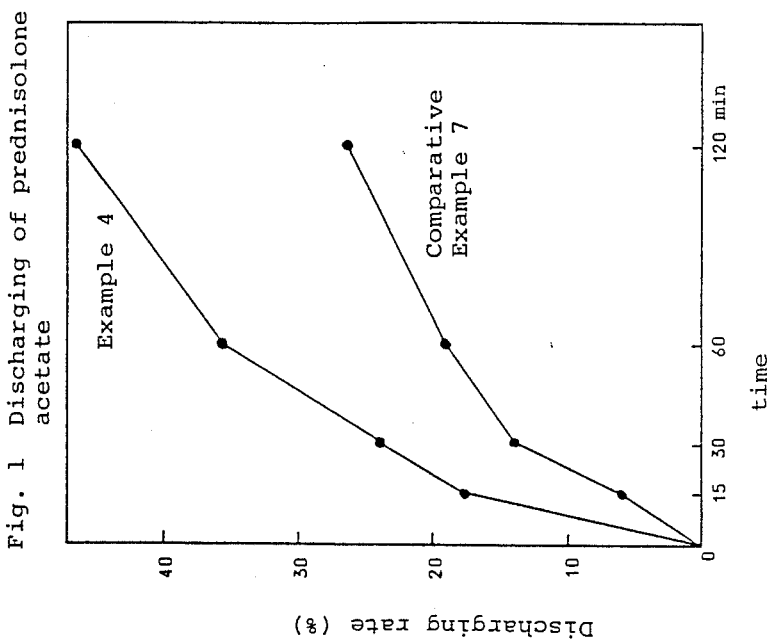
Fig. 1 Discharging of prednisolone acetate

SUPPOSITORY AND BASE THEREOF

This invention relates to a suppository base. More particularly, it relates to a fat composition which has excellent setup characteristics when cast into a container by molding and is highly stable to chemicals.

Suppositories have been employed as means for administering medicines for a long time. Recent developments in suppository bases as well as the techniques for the preparation of the same and clarification of the mechanism of the absorption and metabolism of medicines have made suppositories available not only in topical treatments, for example, at the anus, but also in systemic ones, for example, the administration of contrastimulants and antibiotics. Furthermore, since they exhibit little side effects, suppositories make the administration of the same easy. Therefore, they have been gradually accepted as household medicines of sufficiently wide applications.

STATEMENT OF PRIOR ARTS

A suppository base must have an extremely narrow plastic region, i.e. it should maintain a sufficient hardness in a solid state and rapidly melt around body temperature. Thus cacao butter has been employed therefor. However, cacao butter has some disadvantages in that its high iodine value, i.e., around 34, makes the fat liable to be oxidized when stored for a prolonged period of time, which sometimes results in the inactivation of the medicine. Therefore, fat compositions mainly comprising lauric acid, which show melting properties similar to those of cacao butter, have been widely employed as substitutes therefor. Examples of these compositions are those obtained by blending lauric-type fats such as coconut or palm kernel oil with palm oil and subjecting the mixture to transesterification followed by hardening. Further, there have been disclosed methods for improving the insufficient hardness and setup rate of such a lauric-type fat composition as mentioned above, which comprises removing the glycerides of low molecular weights and low melting points including fatty acids having eight to ten carbon atoms by combining transesterification with molecular distillation (cf. Japanese Patent Publication No. 16594/1984 and No. 16595/1984). However, synthetic fat compositions prepared by fractionally distilling fatty acids of hardened lauric-type fats to thereby remove lower fatty acids and esterifying a mixture of fatty acids mainly having 12 to 18 carbon atoms with a polyhydric alcohol such as glycerol are generally employed. These lauric-type fats have excellent properties as a suppository base, i.e., an appropriate hardness and melting properties, although they have some disadvantages to be overcome.

In the case of a suppository base comprising lauric-type fats having a relatively high hydroxyl value, i.e., more than 20, molten suppository materials may be directly cast into a container and intensely cooled by, for example, ice-cooling. Namely, the supercooling of the base in the cooling step may be prevented and the setup characteristics thereof are relatively good, which makes the modling easy. Such bases as mentioned above have been widely employed in mass-production in factories and the products thus obtained are very firm and exhibit few pinholes and cracking.

However, in the case of a suppository comprising a base having a relatively high hydroxyl value, i.e., more than 20, and containing a medicine having acid group(s) such as aspirin, an increase in the content of free salicyclic acid would inactivate the pharmacological effect of the medicine with the lapse of time. Namely, free hydroxyl groups in the base would catalytically react with readily hydrolyzable medicines such as antibiotics, biochemical preparations and enzymes to thereby result in the separation of these medicines or a decrease in the titer of the same.

Thus, a base of a lower hydroxyl value should be employed in order to prevent the inactivation of these medicines (cf. Japanese Patent Laid-Open No. 52212/1983). It is desirable to use a base having a hydroxyl value of 20 or below, preferably 10 or below. However there is a serious problem in the setup characteristics and workability of the suppositories in this case. That is to say, the poor setup characteristics of a base of a low hydroxyl value significantly lowers the workability of the suppository containing the same in the molding step, i.e., casting and cooling. Further, the supercooling would result in the sedimentation of the medicines during molding and intense cooling such as ice-cooling would bring about some troubles including pinhole and cracking.

As described above, the chemical stability, moldability and workability of lauric-type fats are yet insufficient in spite of the excellent properties of the same as a suppository base. Therefore lauric-type fat bases of low hydroxyl numbers, which have insufficient moldability and workability, are used for medicines liable to be inactivated, e.g., decomposed and discolored, while those having high hydroxyl values are used for relatively stable medicines to thereby enhance the productivity. Namely lauric-type fat bases of different hydroxyl values are employed depending on the medicines at present.

However various medicines have been formulated into suppositories with recent progress in the application of the same. Further it is required to establish techniques for mass-production thereof. Thus it has been demanded to develop a highly effective suppository base having a high chemical stability as well as excellent moldability and workability.

SUMMARY OF THE INVENTION

It is an object of the present invention to provide a suppository base mainly comprising lauric-type fats of a high chemical resistance as well as excellent moldability and workability without causing any deterioration in the physical properties thereof as a suppository base, such as melting properties and hardness. Namely it aims at providing an excellent suppository base of high moldability and workability which has a hydroxyl value of 20 or below, preferably 10 or below, exhibits excellent setup characteristics in molding and shows no trouble such as pinhole or cracking even when subjected to forced cooling such as ice-cooling from an overheated molten state.

In order to achieve the above object, we have examined in detail glyceride compositions mainly comprising diglycerides and forming hydroxyl groups in a lauric-type fat base and consequently found that a suppository base comprising specific lauric-type fats combined with non-lauric-type diglycerides of fatty acids having 14 to 22 carbon atoms has a high chemical stability as well as excellent moldability and workability, thus completing the present invention.

Accordingly the present invention relates to a suppository base which comprises 80 to 99% by weight of lauric-type fat having a hydroxyl value of 20 or below and containing glycerides of fatty acids having 8 to 18 carbon atoms as a main component and 1 to 20% by weight of diglycerides of fatty acids having 14 to 22 carbon atoms. In order to further improve the effect of the suppository base of the present invention, it is desirable to blend 90 to 99% by weight of a lauric-type fat having a hydroxyl value of 10 or below and containing glycerides of fatty acids having 8 to 18 carbon atoms as main components with 1 to 10% by weight of diglycerides of fatty acids having 14 to 22 carbon atoms.

The blending ratio between the lauric-type fat and the non-lauric-type diglyceride constituting the suppository base of the present invention may be varied within the above range without significantly damaging the physical properties thereof required as a suppository base. Further, the fatty acids constituting the lauric-type fat and the non-lauric-type glycerides may be varied to appropriately adjust the physical properties thereof.

The suppository base of the present invention having a hydroxyl value of 20 or below does not inactivate medicines unstable to free hydroxyl groups. When medicines more unstable to hydroxyl groups are to be blended, it is desirable to employ a base of a hydroxyl value of ten or below. In each case, the combination of the lauric-type fat and non-lauric-type glyceride makes the setup characteristics of the base in molding excellent and provides a preferably suppository product showing neither pinholes nor cracking, in spite of the low hydroxyl value of the base.

A suppository base of a hydroxyl value exceeding 20 shows significantly improved setup characteristics compared with a conventional lauric-type fat base having a similar hydroxyl value. However, the former is unavailable in the formulation of a highly decomposable medicine. Thus, the amount of the non-lauric-type diglyceride to be blended into a suppository base should not exceed 20% by weight. On the other hand, a suppository base containing less than 1% by weight of non-laurate diglyceride can not exhibit such excellent moldability and workability as required in the present invention.

The lauric-type fats used as the base of the present invention may be those prepared by treating, for example, hardening, fractionating, transesterifying or distilling raw oils such as coconut, palm kernel or palm oil. In order to further improve the effect of the base of the present invention, it is desirable to employ fats mainly comprising glycerides of saturated fatty acids having 12 to 18 carbon atoms without any lower fatty acid having eight to ten carbon atoms as the lauric-type fats.

The process for the preparation of the non-lauric-type diglyceride constituting the base of the present invention, i.e., the one comprising fatty acids having 14 to 22 carbon atoms is not particularly restricted. A preferable example of the same is as follows. An excessive amount of glycerol is added to a vegetable oil such as palm, soybean or rapeseed oil or a mixture of these hardened oils to thereby perform random transesterification in the presence of an alkaline catalyst. The transesterified fat thus obtained is treated by molecular distillation, column chromatography or solvent fractionation to thereby give the aimed diglyceride product.

The suppository base of the present invention exhibits a sufficient chemical stability as well as excellent moldability and workability without damaging the melting properties and hardness which are required as a base. Namely the suppository base of the present invention gives no trouble such as cracking or pinholes in molding while maintaining a low hydroxyl value. Thus it makes possible, in particular, the mass-production of suppositories comprising chemically unstable medicines.

The suppository base according to the invention is applicable to various suppository preparations such as a steroid hormone, a local anesthetic, an antipyretic analgesic, an antiphlogistic and a drug for controlling intestinal function and constipation.

Pharmacologically effective agents are preferably listed below.

The steroid hormone includes hydrocortisone acetate, hydrocortisone, prednisolone acetate, prednisolone, dexamethasone acetate, dexamethasone, betamethasone, betamethasone valerate and fluocinolone acetonide.

The local anesthetic includes procaine hydrochloride, procaine, lidocaine, lidocaine hydrochloride, dibucaine hydrochloride, dibucaine, cocaine, ethyl aminobenzoate, meprylcaine hydrochloride and hexylcaine hydrochloride.

The antipyretic analgesic includes acetyl salicylic acid (aspirin as a tradename), acetoaminophene, acetophenetidin (phenacetin as a tradename), diclofenac sodium, mefenamic acid, flufenamic acid, choline salicylate, salicyclic amide, aminopyrine, antipyrine, Sulpyrine, phenylbutazone, clofezone, ibuprofen, naproxen, ketoprofen, piroxicam and tiaramide hydrochloride.

The non-steroid antipholgistic includes Allantoin, indomethacin, glycyl-lysine, glycyrrhetic acid, camphor, ichthammol and bufexamac.

The drug for controlling intestinal function and constipation includes sodium pyrosulfate, glycerine, berberine chloride, albumin tannate, berberine tannate and dimethicone.

According to the invention, a medicine is kept stably in the suppository and discharged selectively from the suppository when used. The pharmacological effect depends greatly on the discharging property of a suppository. In this respect, the invention provides an unexpected improvement and enhances the discharging property. Accordingly a medicine contained in the suppository of the invention is well absorbed into the body of a patient and the bioavailability is increased. This is improved in comparison with use of a surfactant such as lecithine and polysorbate.

It is preferable that the suppository contains 0.005 to 0.5 wt. % of a steroid hormone, 0.25 to 5 wt.% of a local anesthetic, 0.5 to 10 wt.% of an antipyretic analgesic, 0.5 to 5 wt.% of a non-steroid antiphlogistic or 0.5 to 10 wt.% of a drug for controlling the intestinal function and constipation.

BRIEF DESCRIPTION OF DRAWINGS

FIGS. 1 and 2 show an improvement of the invention in the discharging property of a medicine contained, proved in Example 4.

The invention will be illustrated in reference with working examples.

EXAMPLE 1 TO 3 AND COMPARATIVE EXAMPLE 1 TO 6

Preparation of Lauric-Type Fat

Lauric-type fat (A): 55 g of lauric acid, 21 g of myristic acid, 9 g of palmitic acid, 15 g of stearic acid and 14 g of glycerol were maintained at 230° C. under a nitrogen atmosphere in the absence of any catalyst for eight hours to thereby perform esterification through dehydration. Then, the water and unreacted fatty acids were removed at a diminished pressure of 1 mmHg at 230° C. to thereby give 103 g of a lauric-type fat (A).

Lauric-type fat (B): 60 g of lauric acid, 21 g of myristic acid, 13 g of palmitic acid, 6 g of stearic acid and 12 g of glycerol were maintained at 230° C. under a nitrogen atmosphere in the absence of any catalyst for eight hours to thereby perform esterification through dehydration. Then the water and unreacted fatty acids were removed at a diminished pressure of 1 mmHg at 230° C. to thereby give 101 g of a lauric-type fat (B).

Lauric-type fat (C): 52 g of lauric acid, 21 g of myristic acid, 10 g of palmitic acid, 17 g of stearic acid and 17 g of glycerol were maintained at 230° C. under a nitrogen atmosphere in the absence of any catalyst for eight hours to thereby perform esterification by dehydration. Then the water and unreacted fatty acids were removed at a diminished pressure of 1 mmHg at 230° C. to thereby give 103 g of a lauric-type fat (C).

Lauric-type fat (D): 0.2 g of sodium methylate was added to an oil composition comprising 91 g of hydrogenated coconut oil having an iodine value of 0.4 and 9 g of hydrogenated palm oil having an iodine value of 0.7. The mixture was stirred in a nitrogen stream at 70° C. for 60 minutes to thereby perform random transesterification. Then it was purified in a conventional manner to thereby give 97 g of a lauric-type fat (D).

Preparation of Diglyceride

Diglyceride (I): 375 g of palm oil having an iodine value of 52.0 and 375 g of hydrogenated palm oil having an iodine value of 0.7 were blended with 250 g of glycerol. 0.1% by weight based on the total system of calcium hydroxide was added thereto and the mixture was stirred under a nitrogen atmosphere at 230° C. for 30 minutes to thereby perform random transesterification. After cooling, the reaction mixture was separated in a separatory funnel and the bottom layer was removed. Then a 10% aqueous solution of citric acid was added and the mixture was stirred and allowed to stand for separation. Then the upper layer was dehydrated and filtered. The random transesterification product thus obtained was passed through a thin-film molecular distillation device at 190° C. and 0.01 mmHg to thereby give 337 g of diglyceride (I) available in the present invention.

Diglyceride (II): 91 g of hydrogenated rapeseed oil having an iodine value of 72.0 and containing 57.2% of trans-acids was blended with 9 g of glycerol. 0.15% by weight based on the total system of sodium methylate was added thereto and the mixture was stirred under a nitrogen atmosphere at 80° C. for 60 minutes to thereby perform random transesterification. The random transesterification product thus obtained was fed to a silica gel column and developed with a mobile phase of hexane and diethyl ether at a weight ratio of 50:50 to thereby give 48 g of diglyceride (II) available in the present invention.

Diglyceride (III): 88 g of hydrogenated palm kernel oil having an iodine value of 0.5 was blended with 12 g of glycerol. 0.15% by weight based on the total system of sodium methylate was added thereto and the mixture was stirred under a nitrogen atmosphere at 80° C. for 60 minutes to thereby perform random transesterification. After the completion of the reaction, the obtained random transesterification product was fed to a silica gel column and developed with a mobil phase of hexane and diethyl ether at a weight ratio of 50:50 to thereby give 44 g of diglyceride (III) to be used for comparison with the present invention.

Table 1 shows the compositions of the diglycerides (I), (II) and (III).

TABLE 1

| | | Composition of diglyceride | | |
|---|---|---|---|---|
| | | Di glyceride (I) | Di glyceride (II) | Di glyceride (III) |
| Glyceride composition (% by wt.) | Monoglyceride | 0.8 | 0.0 | 0.0 |
| | Diglyceride | 85.6 | 96.4 | 97.1 |
| | Triglyceride | 13.6 | 3.6 | 2.9 |
| Fatty acid composition (% by wt.) | Capric acid C8 | — | — | 4.0 |
| | Caprylic acid C10 | — | — | 3.6 |
| | Lauric acid C12 | — | — | 46.2 |
| | Myristic acid C14 | 0.7 | — | 15.6 |
| | Palmitic acid C16 | 44.2 | 4.1 | 8.9 |
| | Stearic acid C18 | 28.1 | 12.2 | 21.4 |
| | Oleic acid C18 F1 | 21.3 | 77.5 | 0.3 |
| | Linolic acid C18 F2 | 5.0 | 0.2 | — |
| | Gadoleic acid C20 F1 | — | 3.0 | — |
| | Erucic acid C22 F1 | — | 2.3 | — |

Note: C18F1 represents an unsaturated fatty acid having one double bond and 18 carbon atoms. Namely, C18Fn represents an unsaturated fatty acid having n double bonds and 18 carbon atoms.

PREPARATION OF SUPPOSITORY BASE

The abovementioned lauric-type fats (A), (B) and (D) were blended with the diglycerides (I) and (II) to prepare suppository bases according to the present invention. Further, lauric-type fats (A), (B), (C) and (D) were employed as comparative examples of suppository bases which have been most widely employed.

TABLE 2

| Preparation of suppository base | |
|---|---|
| | Composition (part by weight) |
| Ex. 1 | lauric-type-fat(A) 95:diglyceride (I) 5 |
| Ex. 2 | lauric-type-fat(B) 90:diglyceride (I) 10 |
| Ex. 3 | lauric-type-fat(D) 93:diglyceride (II) 7 |
| Comp. Ex. 1 | lauric-type-fat(A) 100 |
| Comp. Ex. 2 | lauric-type-fat(B) 100 |
| Comp. Ex. 3 | lauric-type-fat(C) 100 |
| Comp. Ex. 4 | lauric-type-fat(D) 100 |
| Comp. Ex. 5 | cacao butter (iodine number 35) 90:diglyceride (I) 10 |
| Comp. Ex. 6 | lauric-type-fat(B) 90:diglyceride (III) 10 |

MELTING PROPERTIES OF SUPPOSITORY BASE

Table 3 shows the melting properties, which are required as a suppository base, of the suppository bases as prepared above. Table 3 obviously indicates that the melting properties of the suppository bases of Ex. 1 to 3 according to the present invention are sufficiently comparable to those of Comp. Ex. 1 to 4 which are widely used at present. Namely, the suppository bases comprising specific lauric-type fats and non-lauric-type glycerides of the present invention never damage sharp melting properties nor appropriate hardness.

On the other hand, when the non-lauric-type diglyceride is blended with cacao butter, which is a typical non-lauric-type fat, in place of the lauric-type fats, which is another component of the present invention, the melting properties showed a significant decrease (cf.

Comp. Ex. 5). Namely, the hardness is insufficient inspite of its melting point in this case. Further, the relatively high iodine value, i.e., around 34, thereof makes it oxidation stability poor.

TABLE 3

| Suppository base | Melting properties of suppository base | | | | |
|---|---|---|---|---|---|
| | m.p. (°C.) | Solid fat content (% by wt.) | | | |
| | | 25.0° C. | 30.0° C. | 32.5° C. | 35.0° C. |
| Ex. 1 | 35.2 | 87 | 69 | 36 | 4 |
| Ex. 2 | 35.6 | 88 | 70 | 38 | 6 |
| Ex. 3 | 34.9 | 64 | 47 | 21 | 5 |
| Comp. Ex. 1 | 35.2 | 87 | 67 | 35 | 4 |
| Comp. Ex. 2 | 34.5 | 90 | 73 | 40 | 3 |
| Comp. Ex. 3 | 34.8 | 72 | 55 | 23 | 6 |
| Comp. Ex. 4 | 35.2 | 61 | 45 | 20 | 4 |
| Comp. Ex. 5 | 36.4 | 62 | 38 | 21 | 11 |
| Comp. Ex. 6 | 34.8 | 83 | 66 | 36 | 3 |

Note: m.p.: according to the Pharmacopoeia of Japan.
Solid fat content: determined by pulse NMR.

Moldability Test of Suppository Base

The suppository bases of Examples 1 to 3 each comprising lauric-type fat and non-lauric-type diglyceride, those of Comparative Examples 1 to 4 widely applied at present and that of Comparative Example 6 comprising lauric-type fat and lauric-type diglyceride showed sufficient melting properties. Suppositories were molded with the use of these bases. That is, each base was completely molten at 45° C. and 8% by weight of aspirin was added thereto. The obtained mixture was cooled to 40° C. under stirring. 1.9-g portions of the suppository composition dissolved and dispersed at 40° C. were poured into plastic suppository containers and rapidly cooled therein to 5° C. and 20° C. to thereby give molded suppositories. 100 molded products prepared from each base were taken out of the containers and the surface of each product was observed. Cracked or damaged ones and those showing pinholes were counted and the moldability and workability were evaluated therefrom. Table 4 shows the result.

TABLE 4

| Suppository base | Hydroxyl value | Moldability and workability test of suppository | | | | | |
|---|---|---|---|---|---|---|---|
| | | Number of inferior ones per 100 and condition | | | | | |
| | | 40° C. → 5° C. | | | 40° C. → 20° C. | | |
| | | Damaged | Pin-hole | Surface condition | Damaged | Pin-hole | Surface condition |
| Ex. 1 | 18 | 0 | 0 | ⊙ | 0 | 0 | ⊙ |
| Ex. 2 | 7 | 2 | 0 | ⊙ | 0 | 0 | ⊙ |
| Ex. 3 | 10 | 0 | 0 | ⊙ | 0 | 0 | ⊙ |
| Comp. Ex. 1 | 15 | 49 | 100 | X | 34 | 91 | X |
| Comp. Ex. 2 | 2 | 52 | 100 | X | 38 | 88 | X |
| Comp. Ex. 3 | 39 | 1 | 65 | ○ | 0 | 24 | ○ |
| Comp. Ex. 4 | 5 | 7 | 100 | X | 2 | 97 | Δ |
| Comp. Ex. 6 | 8 | 27 | 100 | X | 25 | 80 | X |

Note: Surface condition
⊙: glossy and dense
○: unglossy and dense
Δ: unglossy and partly spotted
X: unglossy and entirely spotted The result as shown in Table 4 suggests that the suppository bases of the present invention gave products of excellent qualities, having glossy and uniform surface and showing little cracking and pinholes even when subjected to forced cooling. On the other hand, conventional ones comprising lauric-type fat alone gave suppositories of insufficient qualities, although those having higher hydroxyl values showed some improvement. In the case of the suppository base prepared by blending lauric-type fats with lauric-type diglycerides mainly comprising lauric acid, the obtained suppository had insufficient qualities (cf. Comparative Example 6). Thus the suppository base of the present invention comprising specific lauric-type fats and non-lauric-type diglycerides can give suppositories of excellent moldability and workability.

CHEMICAL STABILITY TEST

The molded suppositories obtained in the molding test of the suppository bases as mentioned above were stored in thermostats at 20° C. and 40° C. for six months. Then the content of salicylic acid in each suppository was determined by high-performance liquid chromatography in order to examine the extent of the decomposition of aspirin. Table 5 shows the result.

TABLE 5

| Suppository base | Hydroxyl value | Chemical stability of molded suppository | | |
|---|---|---|---|---|
| | | Salicylic acid content (% by wt.) | | |
| | | Before storage | Stored at 20° C. for 6 m. | Stored at 40° C. for 6 m. |
| Ex. 1 | 18 | 0.00 | 0.63 | 5.97 |
| Ex. 2 | 7 | 0.00 | 0.43 | 5.13 |
| Ex. 3 | 10 | 0.00 | 0.53 | 6.01 |
| Comp. Ex. 1 | 15 | 0.00 | 0.59 | 5.86 |
| Comp. Ex. 2 | 2 | 0.00 | 0.50 | 6.01 |
| Comp. Ex. 3 | 39 | 0.00 | 2.45 | 16.97 |
| Comp. Ex. 4 | 5 | 0.00 | 0.49 | 5.33 |
| Comp. Ex. 6 | 8 | 0.00 | 0.48 | 5.88 |

EXAMPLE 4 AND COMPARATIVE EXAMPLE 7

A suppository was produced with a suppository container, using a suppository base (Y) of lauric-type triglyceride and 10 wt.% of diglyceride, corresponding to the base of Example 2, and 1 mg of prednisolone acetate and 5 mg of dibucaine hydrochloride per one suppository. A control suppository was prepared in the same way as above, except that lauric-type triglyceride only was used as a base (X). A discharging test was effected with these suppositories. A sample of 1 ml was taken out in 15, 30, 60 and 120 minutes and analyzed with the high speed liquid chlomatography. The test was repeated twice and results were obtained on the average of the two tests and are shown in Table 6 and 7 and FIGS. 1 and 2.

TABLE 6

Discharging of prednisolone acetate

| time (min) | Comparative Example 7 base (X) discharging | | Example 4 base (Y) discharging | |
| --- | --- | --- | --- | --- |
|  | amount (μg) | rate (%) | amount (μg) | rate (%) |
| 15 | 62.5 | 6.25 | 173.0 | 17.30 |
| 30 | 140.0 | 14.00 | 234.0 | 23.40 |
| 60 | 187.5 | 18.75 | 350.5 | 35.05 |
| 120 | 262.0 | 26.20 | 480.0 | 48.00 |

TABLE 7

Discharging of dibucaine hydrochloride

| time (min) | Comparative Example 7 base (X) discharging | | Example 4 base (Y) discharging | |
| --- | --- | --- | --- | --- |
|  | amount (μg) | rate (%) | amount (μg) | rate (%) |
| 15 | 313.5 | 6.27 | 504.0 | 10.08 |
| 30 | 421.0 | 8.42 | 563.5 | 11.27 |
| 60 | 496.0 | 9.92 | 722.0 | 14.44 |
| 120 | 569.0 | 11.38 | 858.0 | 19.16 |

EXAMPLE 5

A suppository composition for hemorrhoids was prepared, using 1 mg of prednisolone acetate, 5 mg of dibucaine hydrochloride, 20 mg of tocopherol acetate, 100 mg of zinc oxide and 1474 mg of the base Y of hard fat per suppository. The composition was heated up to 60° C. and blended. It was introduced by 1.6 g into a plastic container for suppositories, cooled and moulded. The suppository was administered to 30 patients of with hemorrhoids every morning and every night before they went to bed for ten days. Changes in the patients were observed. Results are shown in Table 8. It is noted that the composition was useful for treating hemorrhoids.

TABLE 8

Clinical results of the suppository

| conditions | | before use | after use |
| --- | --- | --- | --- |
| pain | always feeling | 7 | 0 |
|  | feeling when the body moves | 56 | 19 |
|  | feeling on evacuation | 28 | 21 |
|  | no | 19 | 60 |
| bleeding | very badly | 10 | 0 |
|  | some drops | 42 | 22 |
|  | attaching to paper | 45 | 23 |
|  | no | 3 | 55 |
| swelling | very badly | 22 | 8 |
|  | considerably | 37 | 26 |
|  | slightly | 41 | 37 |
|  | not | 0 | 29 |
| itching | very badly | 0 | 0 |
|  | considerably | 11 | 0 |
|  | slightly | 33 | 17 |
|  | not | 56 | 83 |

Results are shown in terms of a percent of persons having the condition.

What is claimed is:

1. A suppository base which comprises 80 to 99 percent by weight of a fat composition, said fat composition having a hydroxyl value of 20 or lower and containing glycerides of fatty acids having 12 to 18 carbon atoms, and 1 to 20 percent by weight of diglycerides of fatty acids having 14 to 22 carbon atoms, with the proviso that said diglycerides do not contain a lauric acid moiety.

2. A suppository base as claimed in claim 1, which comprises 90 to 99 percent by weight of said fat composition and 1 to 10 percent by weight of said diglycerides.

3. A suppository base as claimed in claim 2, in which said fat composition has a hydroxyl value of 10 or lower.

4. A suppository which comprises the suppository base as defined in claim 1 and a pharmacologically effective amount of a pharmacologically effective compound.

5. A suppository as claimed in claim 4, in which said pharmacologically effective compound is selected from the group consisting of steroid hormones, local anesthetics, antipyretic analgesics, nonsteroid antiphlogistics and drugs for controlling the intestinal function and constipation.

6. A suppository base as claimed in claim 1, in which said fat composition has a hydroxyl value of 10 or lower.

7. A suppository base as claimed in claim 1, wherein said fat composition consists essentially of glycerides of fatty acids selected from the group consisting of lauric acid, myristic acid, palmitic acid, stearic acid and mixtures thereof.

8. A suppository base as claimed in claim 1, wherein said diglycerides are formed from fatty acids selected from the group consisting of myristic acid, palmitic acid, stearic acid, oleic acid, linolic acid, gadoleic acid, erucic acid and mixtures thereof.

9. A suppository base which consists of 90 to 95 percent by weight of a fat composition, said fat composition having a hydroxyl value of 20 or lower and consisting essentially of glycerides of fatty acids selected from the group consisting of lauric acid, myristic acid, palmitic acid, stearic acid and mixtures thereof, and 5 to 10 percent by weight of diglycerides formed from fatty acids selected from the group consisting of myristic acid, palmitic acid, stearic acid, oleic acid, linolic acid, gadoleic acid, erucic acid and mixtures thereof.

* * * * *